United States Patent
Madey

(10) Patent No.: US 11,576,706 B2
(45) Date of Patent: Feb. 14, 2023

(54) CHEST WALL REPAIR DEVICE

(71) Applicant: Revelation Plating, LLC, Clackamas, OR (US)

(72) Inventor: Steven Madey, Portland, OR (US)

(73) Assignee: REVELATION PLATING, LLC, Clackamas, OR (US)

( * ) Notice: Subject to any disclaimer, the term of this patent is extended or adjusted under 35 U.S.C. 154(b) by 79 days.

(21) Appl. No.: 17/307,665

(22) Filed: May 4, 2021

(65) Prior Publication Data

US 2021/0251671 A1 Aug. 19, 2021

Related U.S. Application Data

(62) Division of application No. 16/315,107, filed as application No. PCT/US2017/041573 on Jul. 11, 2017.

(60) Provisional application No. 62/360,633, filed on Jul. 11, 2016.

(51) Int. Cl.
*A61B 17/80* (2006.01)
*A61B 17/00* (2006.01)
*A61B 17/68* (2006.01)

(52) U.S. Cl.
CPC ...... *A61B 17/8085* (2013.01); *A61B 17/8076* (2013.01); *A61B 2017/00862* (2013.01); *A61B 2017/681* (2013.01)

(58) Field of Classification Search
CPC ............ A61B 17/8085; A61B 17/8076; A61B 17/823; A61B 17/80; A61B 2017/00862; A61B 2017/681
See application file for complete search history.

(56) References Cited

U.S. PATENT DOCUMENTS

| | | | |
|---|---|---|---|
| 8,226,693 B2* | 7/2012 | Reimels | A61B 17/8004 606/282 |
| 2003/0023311 A1 | 1/2003 | Trieu | |
| 2006/0122611 A1 | 6/2006 | Morales et al. | |
| 2007/0239158 A1* | 10/2007 | Trieu | A61B 17/7059 606/279 |
| 2008/0154312 A1 | 6/2008 | Colleran et al. | |
| 2012/0271311 A1 | 10/2012 | Hearn | |
| 2013/0060288 A1* | 3/2013 | Rodgers | A61B 17/808 606/283 |

(Continued)

FOREIGN PATENT DOCUMENTS

| | | |
|---|---|---|
| WO | 2004-096068 | 11/2004 |
| WO | 2010-004602 | 1/2010 |
| WO | 2013-130978 | 9/2013 |

OTHER PUBLICATIONS

Franklin International; "Wood Adhesives, Advantage FJ-430—Product Data Sheet"; www.franklinadhesivesandpolymers.com; Feb. 15, 2022.

*Primary Examiner* — Zade Coley
*Assistant Examiner* — Tracy L Kamikawa
(74) *Attorney, Agent, or Firm* — Schwabe, Williamson & Wyatt, P.C.

(57) ABSTRACT

Embodiments herein provide a chest wall repair plate device where a central portion of the device is comprised of an elastomer to allow for rapid resection using a standard surgical scalpel should there be a need to quickly re-enter the chest cavity. The elastomeric section adjoins two or more rigid plate sections creating a simple, easily removable sternal stabilization system.

8 Claims, 8 Drawing Sheets

(56) References Cited

U.S. PATENT DOCUMENTS

| | | | |
|---|---|---|---|
| 2015/0018830 A1* | 1/2015 | Knoepfle | A61B 17/8057 606/71 |
| 2015/0045794 A1* | 2/2015 | Garcia | A61B 17/82 606/74 |
| 2015/0352278 A1 | 12/2015 | Lechmann et al. | |
| 2016/0376893 A1 | 12/2016 | Hardwicke et al. | |

* cited by examiner

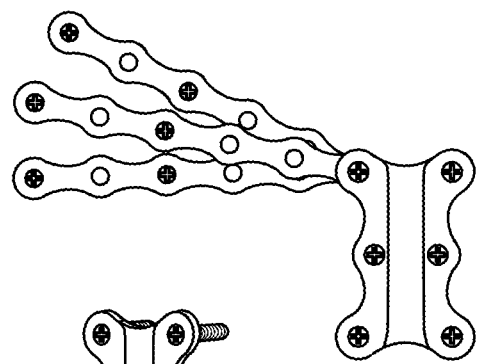
FIG. 7A
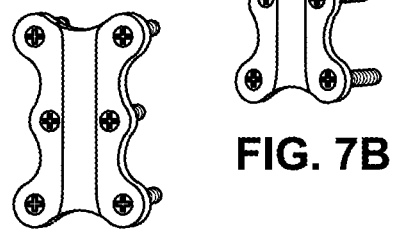
FIG. 7B
FIG. 7C
FIG. 7D
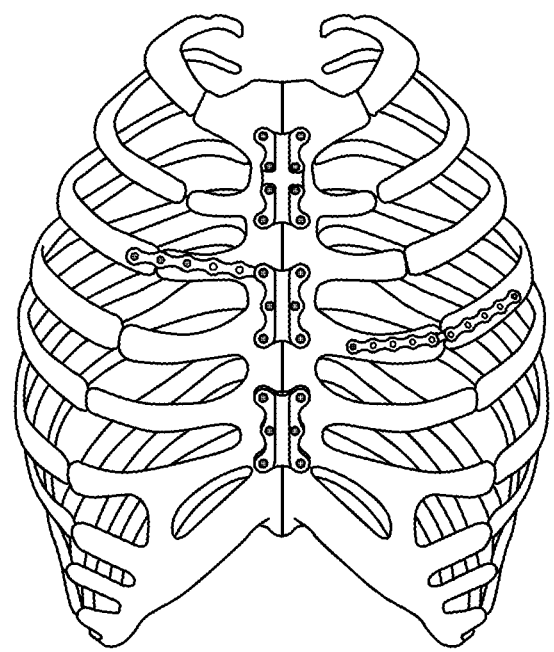
FIG. 8

CHEST WALL REPAIR DEVICE

CROSS REFERENCE TO RELATED APPLICATION

The present application is a Divisional application of U.S. patent application Ser. No. 16/315,107 filed Jan. 3, 2019 which is a national phase entry under 35 U.S.C. § 371 of International Application No. PCT/US2017/041573, filed Jul. 11, 2017, entitled "CHEST WALL REPAIR DEVICE," which designated, among the various States, the United States of America, and which claims priority to U.S. Provisional Patent Application No. 62/360,633, filed Jul. 11, 2016, all of which are hereby incorporated by reference.

TECHNICAL FIELD

Embodiments herein relate to a chest wall repair device, such as for use in stabilization of a sternal osteotomy or for a stabilizing a rib segment.

BACKGROUND

The sternum is a bony structure that connects ribs at the front of the chest wall. A sternotomy is a surgical procedure in which the sternum is cut along its longitudinal midline. A sternotomy is performed to gain access to the thoracic cavity for surgery on the heart, lung or other inner organs.

After a sternotomy has been performed, the divided sternum must be reconnected, or "closed," in a sufficiently stable manner to allow for bony healing of the sternotomy cut. Closure of a sternal osteotomy has traditionally been performed using stainless steel wires that are circumferentially wrapped around the sternum or through the sternum. The circumferential cerclage wires are tensioned to compress the opposing sides of the divided sternum against each other. This traditional cerclage wire technique for sternotomy closure can exhibit healing complications caused by deficient stabilization due to loose or broken wires. Especially in older patients with weaker bone, the thin steel wires can gradually cut through the sternum and loosen. Moreover, circumferential cerclage wiring is time-consuming and complicated, since it requires routing of multiple wires around the back of the sternum.

To provide a simpler and more durable fixation, metallic plates and clamps for sternal closure have been developed that attach to the front of the sternum. Clinical studies have shown that compared to traditional wire cerclage, repair of a sternal osteotomy with plates provides more stable fixation and leads to better healing, whereby patients experience less pain and require less narcotic medication.

Moreover, sternal plates and clamps generally do not require surgical access to the back of the sternum, and eliminate the application of circumferential wires or ties. However, their removal typically requires special instruments and extraction of fixation screws, whereby screw heads are frequently overgrown by soft tissue or damaged during implant insertion, complicating screw removal. The speed and ease of implant removal is critical when emergency surgical re-access is required in patients who incur a life-threatening complication. Any delay during emergent re-entry of the thoracic cavity caused by removal of a sternal plate or clamp can therefore be life-threatening, especially in case of heart failure or hemorrhagic bleeding.

In addition, other aspects of the chest wall may need to be repaired in addition to, or independent of, the sternum, such as caused by injury or other damage or by rib resection.

BRIEF DESCRIPTION OF THE DRAWINGS

Embodiments will be readily understood by the following detailed description in conjunction with the accompanying drawings and the appended claims. Embodiments are illustrated by way of example and not by way of limitation in the figures of the accompanying drawings.

FIGS. 7A, 7B, 7C, and 7D illustrate examples of various embodiments of chest wall repair devices for fixing the sternum and/or a rib segment; and FIG. 8 illustrates the chest wall repair devices of FIGS. 7A, 7B, 7C, and 7D in example locations on the chest wall.

DETAILED DESCRIPTION OF DISCLOSED EMBODIMENTS

Figure 1A:
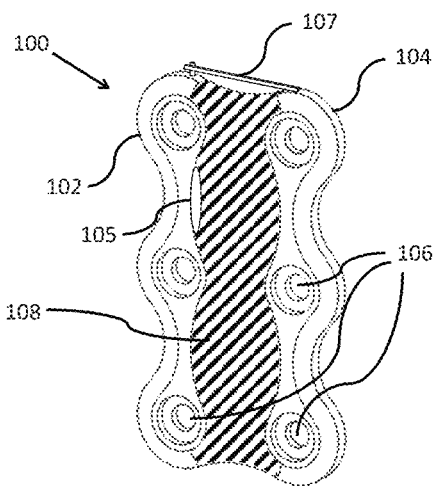
FIG. 1A illustrates a perspective view of one embodiment of a sternal repair device in accordance with embodiments herein.

In the following detailed description, reference is made to the accompanying drawings that form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense.

Various operations may be described as multiple discrete operations in turn, in a manner that may be helpful in understanding embodiments; however, the order of description should not be construed to imply that these operations are order-dependent.

The description may use perspective-based descriptions such as up/down, back/front, and top/bottom. Such descriptions are merely used to facilitate the discussion and are not intended to restrict the application of disclosed embodiments.

The terms "coupled" and "connected," along with their derivatives, may be used. It should be understood that these terms are not intended as synonyms for each other. Rather, in particular embodiments, "connected" may be used to indicate that two or more elements are in direct physical contact with each other. "Coupled" may mean that two or more elements are in direct physical contact. However, "coupled" may also mean that two or more elements are not in direct contact with each other, but yet still cooperate or interact with each other.

For the purposes of the description, a phrase in the form "A/B" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

The description may use the terms "embodiment" or "embodiments," which may each refer to one or more of the same or different embodiments. Furthermore, the terms "comprising," "including," "having," and the like, as used with respect to embodiments, are synonymous, and are generally intended as "open" terms (e.g., the term "including" should be interpreted as "including but not limited to," the term "having" should be interpreted as "having at least," the term "includes" should be interpreted as "includes but is not limited to," etc.).

With respect to the use of any plural and/or singular terms herein, those having skill in the art can translate from the plural to the singular and/or from the singular to the plural as is appropriate to the context and/or application. The various singular/plural permutations may be expressly set forth herein for sake of clarity.

To alleviate the clinical challenges noted above, the present disclosure connects two or more plate sections by a central elastomeric portion that can readily be bisected for rapid reentry. Moreover, the invention may also be practiced for fixation of rib fractures or for spanning of rib defects or resections, whereby the central elastomeric portion enables fitting adjacent plate sections to the trajectory of the curved ribs. This elastic connection can furthermore shield the adjacent plate sections from stress and fatigue by allowing elastic flexion.

In embodiments, the present disclosure addresses the critical need for fast and simple reentry of the chest cavity by provision of a sternal plate with an elastomeric midsection. This mid-section can readily be cut with the same scalpel used for skin incision. Assuming the sternum has not fully healed after an osteotomy, cutting of the elastomeric mid-section instantly enables separation of the osteotomized sternum and permits emergency access to the thoracic cavity without requiring special instruments.

In various embodiments, methods, apparatuses, and systems for repair of a sternum after sternal osteotomy that allows for rapid resection is provided. Embodiments herein employ a novel technique where a central portion of the device is comprised of an elastomer to allow for rapid resection using a standard surgical scalpel should there be a need to quickly re-enter the chest cavity. Previous attempts have employed strategies such as removable metallic locking pins or thin struts or wires that could be cut to allow for rapid re-entry. Others have used multi-component clamps or polymer ties to achieve removable fixation. However, these methods create additional complexity and require additional instrumentation for resection.

While embodiments herein may use the term "central" to describe the location of the elastomer, it should be understood that the term does not necessarily mean that the elastomer is at or along one or more center lines of the device. Rather, the term "central" refers to an arrangement whereby elastomer is at least partially flanked by the supporting plate sections.

Embodiments herein utilize a plate design that is comprised of a plurality of bone fixation sections that are intended to be fixed to the sternum or a rib section and joined by an elastomer section. The bone fixation sections are affixed to bone by threaded fixation members or by geometric constraint such as a hook. The elastomer section is intended to provide a pathway by which a surgeon can cut the plate to separate portions of the plate in order to access and re-open the chest cavity, should the need arise. In embodiments, the presence of elastomer may also provide a degree of flexibility regarding the angle or orientation of the fixation construct on the bone.

In some embodiments the bone fixation sections may have a feature to engage a spreading instrument to pre-stretch the elastomeric section by increasing the distance between the two bone fixation sections prior to insertion of the threaded fixation members. By pre-stretching the elastomeric section during fixation, compression can be achieved between the sternum or other bone halves after release of the instrument.

The width of the elastomer section and the elastic modulus of the elastomer material can be varied to affect the amount of motion between the two plate sections. In some embodiments, the elastomer section may be comprised of multiple elastomer materials or grades to achieve different mechanical properties in different regions. Suitable materials for the elastomeric section/portion include silicone or thermoplastic elastomers such as polyurethanes. Should it be desirable to visualize the elastomeric material on the chest x-rays, a radiopaque powder can be added to the elastomer during molding or radiopaque markers such as spheres can be inserted into the elastomer during manufacture. A suitable elastomeric material may have a modulus between 0.1-50 MPa. The elastomeric section should be similar in thickness to the plate, which is typically between 1-4 mm in thickness. The elastomeric section should be between 1-5 mm wide to allow for easy insertion of a scalpel.

In various embodiments, there are two bone fixation sections each with a plurality of receiving holes. In other embodiments, there may be multiple fixation sections each with a single or plurality of receiving holes.

In various embodiments, the bone fixation sections are comprised of a metallic biocompatible material such as titanium or stainless steel, but may also be comprised of a polymeric material such as PEEK (polyetheretherketone). In various embodiments, the bone fixation sections may be affixed to only the sternum or to both the ribs as well as the sternum to achieve greater fixation. When used, rib fixation may be on only one side, or may be on both sides of the sternum.

In various embodiments, the elastomeric section is adhered/secured to the bone fixation sections to form a single piece (unitary) device. Adhesion can be achieved during the molding process by mechanical interlocking of the elastomeric material around features on the surface of the metal parts or chemical adhesion to the surface of the metallic parts. In some cases, a primer can be applied to the metal parts to provide a more chemically favorable surface for bonding of the elastomeric material.

In some embodiments, the elastomeric section may be separate from the bone fixation sections, and affixed using a clip mechanism or other type of mechanical constraint. Making the elastomeric section separate would allow for rapid replacement of the elastomeric section without necessitating removing and replacing the bone fixation sections.

In various embodiments, features may be provided that restrain the maximal extension of the elastomer or serve to prevent the plate segments from gross separation thus providing a redundancy safety feature in case the elastomer should fail. In embodiments, a central elastomeric portion may contain a connection between the plate sections comprised of one or more elongated polymeric fibers. In other embodiments, at least one plate section may have an extending feature or hook, such as locking bar 107 in FIG. 1A) that selectively, mechanically interlocks within the opposing plate section and constrains the lateral motion or separation of the plate sections.

In embodiments, a central elastomeric portion may incorporate voids/spaces (such as void 104 in FIG. 1A) at the elastomer/plate interface that act to prevent propagation of delamination of the elastomer from the plate.

Figure 1B:
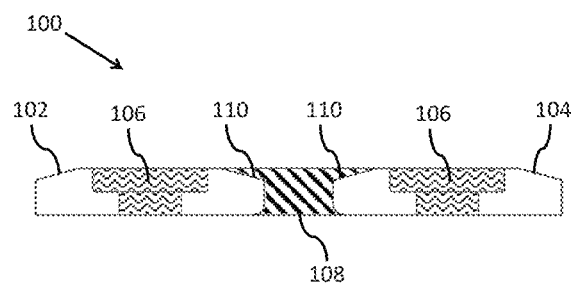
FIG. 1B is a cross-sectional view of the device of FIG. 1A, better illustrating the central elastomer portion disposed between the two plate sections in accordance with embodiments herein.
Figure 1C:
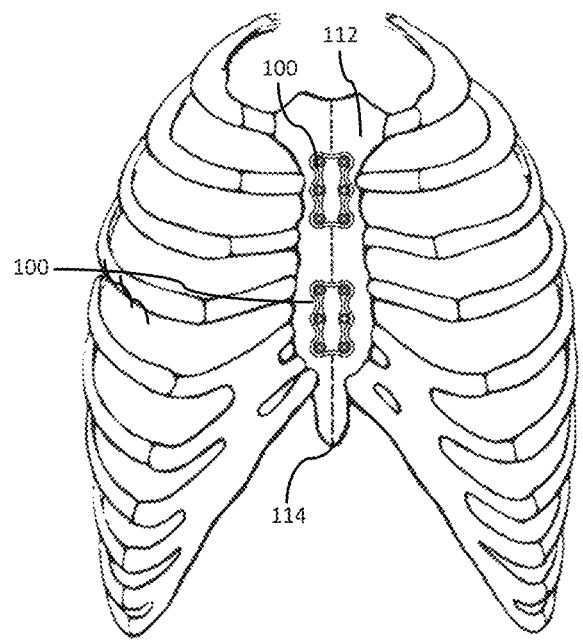
FIG. 1C is a view of the sternal repair device of FIG. 1A in place on a sternum in accordance with embodiments herein.

The sternal repair device 100 shown in FIGS. 1A-1C is comprised of left and right plate sections 102, 104 intended to be affixed to a sternum on opposing sides of a sternal osteotomy. Each plate section incorporates multiple receiving holes 106 for threaded fixation members, with the two plate sections joined by a central elastomer portion 108 that is coupled to both plate sections to form a unitary device. Although not shown in the illustrated embodiment, the receiving holes may be threaded in order to engage threads along a portion of the threaded fixation member, such as a bone screw. A feature of this embodiment is that the central elastomer portion comprises a path by which a surgeon can rapidly bisect the sternal repair device using a scalpel should re-resection of the sternum be necessary.

FIG. 1B shows a cross-sectional view of device 100, where the elastomer 108 is located between and bonded to the plate sections 102, 104 at two interfaces 110, which would prevent substantial contact between the plate sections.

FIG. 1C shows an anterior view of the chest wall and illustrates a suitable placement of a pair of the sternal repair devices 100 on the sternum 112 as well as an anticipated sternal resection line 114. The device is intended to be placed on the sternum after an osteotomy and fixed to the sternum using threaded fixation members, such as bone screws. In some cases, multiple plates be used to fully secure the sternum, and/or they can be used in conjunction with other fixation devices.

Figure 2A:
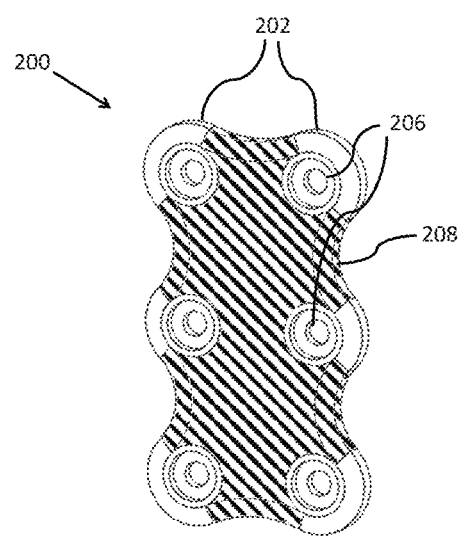
FIG. 2A is a perspective view of another embodiment of a sternal repair device where the screw hole plate sections are discrete elements in accordance with embodiments herein.
Figure 2B:
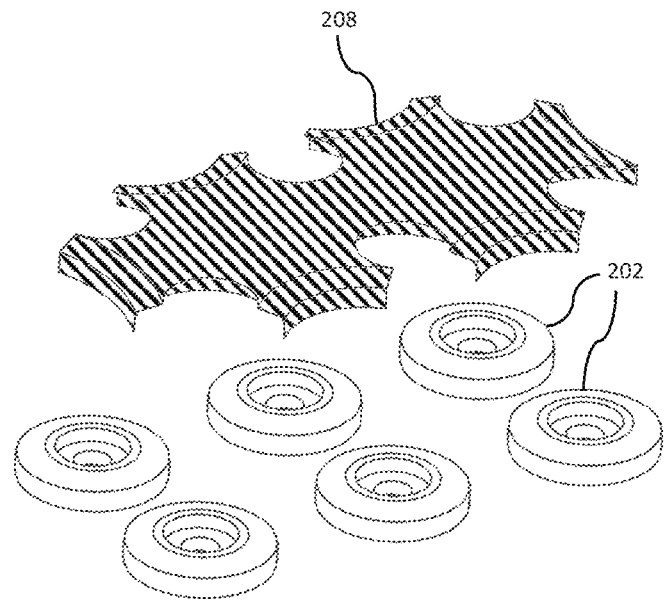
FIG. 2B is an exploded view of the device of FIG. 2A showing the discrete elements separated from the central elastomer portion in accordance with embodiments herein.

FIG. 2A shows a perspective view of an alternate embodiment where the sternal repair device 200 comprises a plurality of plate sections 202 that incorporate receiving holes 206 for threaded fixation members joined by a central elastomer portion 208 that is coupled to the plate sections. FIG. 2B shows an exploded view where the individual plate sections 202 are shown separated from the elastomer portion 208. The plurality of plate sections allow the device to better conform to the topography of the sternum as there is flexibility about both the longitudinal and lateral axes of the device. In this embodiment, the elastomer still comprises a path by which a surgeon can rapidly bisect the device using a scalpel should re-resection of the sternum be necessary.

Figure 3A:
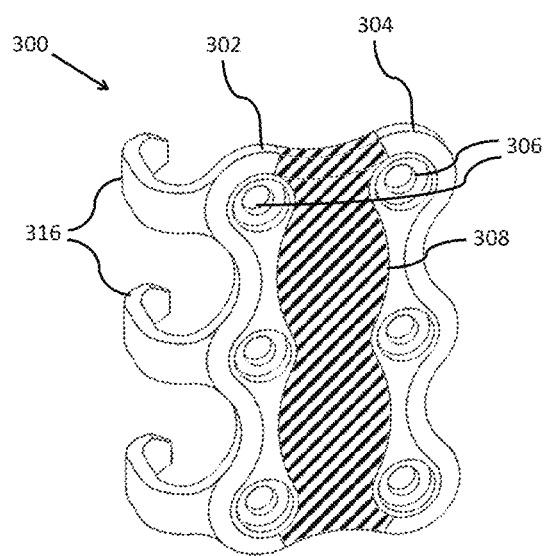
FIG. 3A is a perspective view of another embodiment that incorporates protruding hooks that can wrap over the edge of the sternum in accordance with embodiments herein.
Figure 3B:
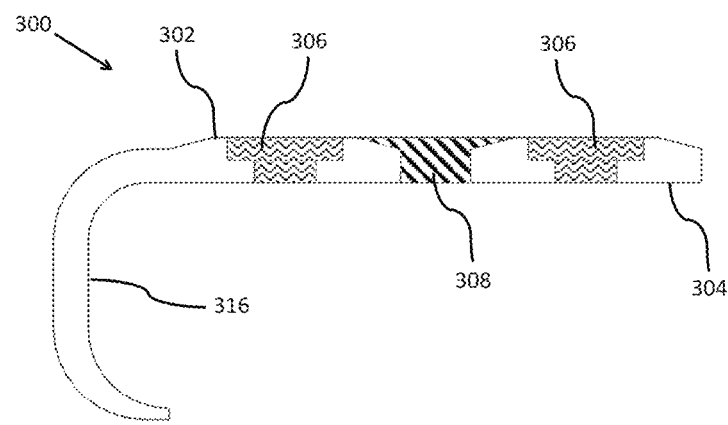
FIG. 3B is a cross-sectional view of the device of FIG. 3A showing the hooks in accordance with embodiments herein.
Figure 3C:
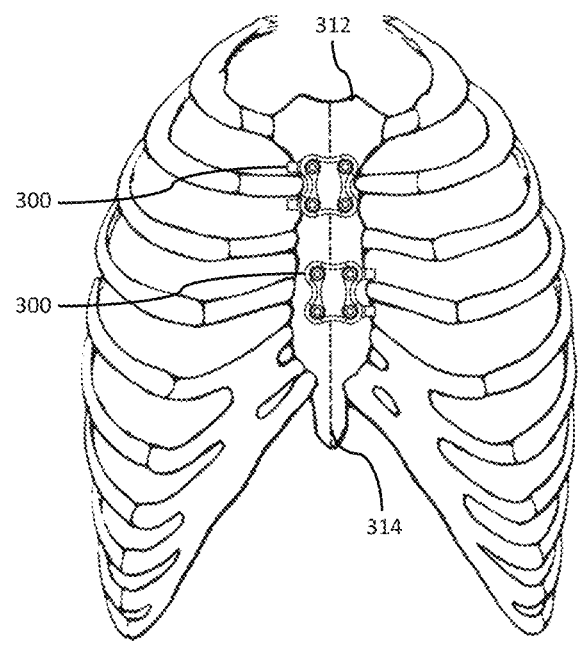
FIG. 3C is a view of the device of FIG. 3A in place on a sternum in accordance with embodiments herein.

FIG. 3A shows a perspective view of an alternate embodiment of the sternal repair device 300 that is comprised of two plate sections 302, 304 that have receiving holes 306 for threaded fixation members joined by a central elastomer portion 308 that is coupled to both plate sections. Plate section 302 has a plurality of hooks 316 that are intended to engage the edge of the sternum between the ribs to provide additional stability to the device fixation or which can be used in lieu of threaded fixation members on that side of the sternal resection. FIG. 3B is a cross-sectional profile view of sternal repair device 300 illustrating hooks 316 on plate section 302. FIG. 3C shows an anterior view of the chest wall illustrating placement of a pair of hooked sternal repair devices 300 on the sternum 312 as well as an anticipated sternal resection line 314. While FIGS. 3A-3C show devices with two or three hooks, any suitable number of hooks may be used, whether 1, 2, 3, 4, or more as appropriate for the particular application.

Figure 4A:
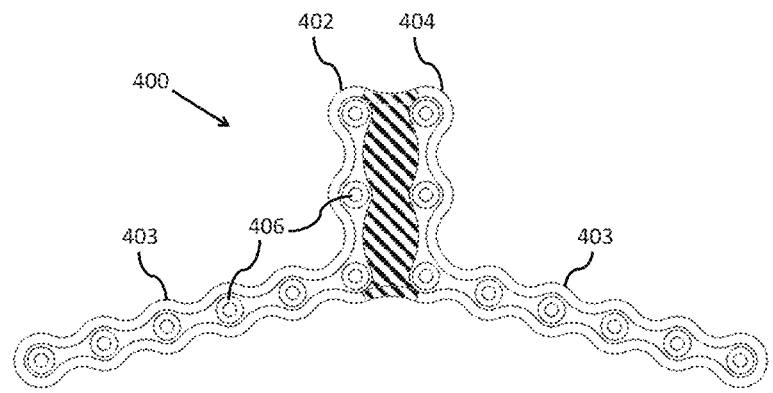
FIG. 4A is a view of another embodiment where the plate sections also engage a portion of the ribs in accordance with embodiments herein.
Figure 4B:
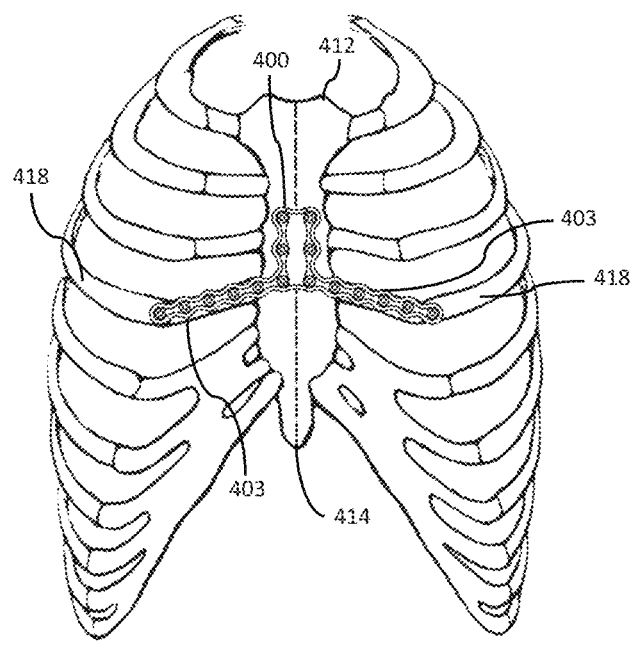
FIG. 4B is a view of the device of FIG. 4A in place on a sternum.

FIG. 4A is a front view of an alternate embodiment of a sternal fixation device 400 similar to the embodiment described in FIG. 1A but where the plate sections 402, 404 extend to couple with the sternum 412 and the rib portion 418 (see FIG. 4B) with receiving holes 406 for threaded fixation members present along the sternal plate and the extension 403. FIG. 4B shows an anterior view of the chest wall illustrating placement of a sternal repair device 400 on the sternum 412 along an anticipated sternal resection line 414 with plate extensions 403 that are fixed to the ribs 418.

Figure 5A:
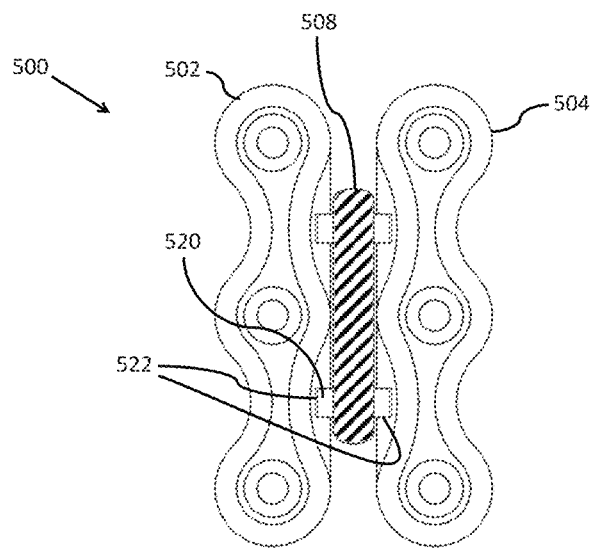
FIG. 5A is a front view of an alternate embodiment where the elastomeric section is separate from the plates and attaches by means of clips in accordance with embodiments herein.
Figure 5B:
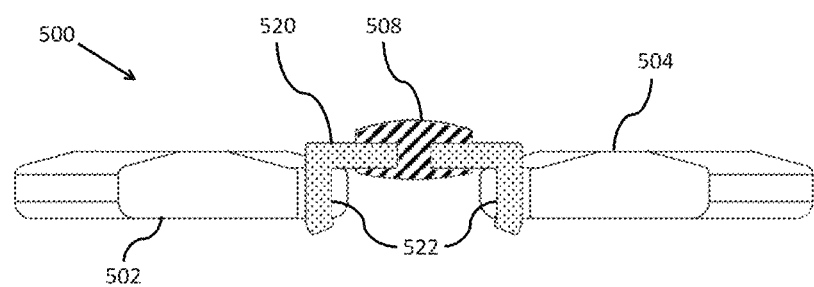
FIG. 5B is a cross-sectional view of the device of FIG. 5A showing the elastomer disposed around the clips that engage cavities in the plates in accordance with embodiments herein.

FIG. 5A shows a front view of an alternate embodiment of the sternal fixation device 500 where the elastomer section 508 is separate from the two plate sections 502, 504, but is affixed to the plate sections by means of clips 520 that are integral to the elastomer and interact with cavities 522 in the plate sections. FIG. 5B shows a cross-sectional view of the plate sections 502, 504, clips 520, and elastomer section 508 showing one method of embedding the clips within the elastomer and engaging the clips within the cavities of the plate sections.

Figure 6A:
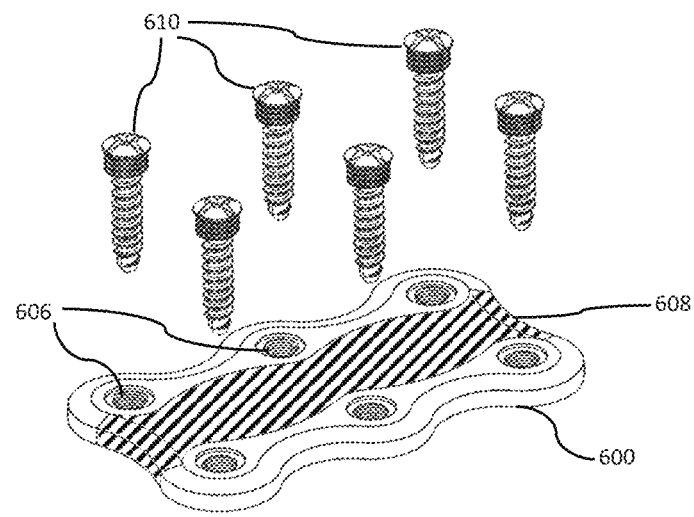
FIG. 6A is an exploded view of a sternal fixation device and threaded fasteners in accordance with embodiments herein.
Figure 6B:
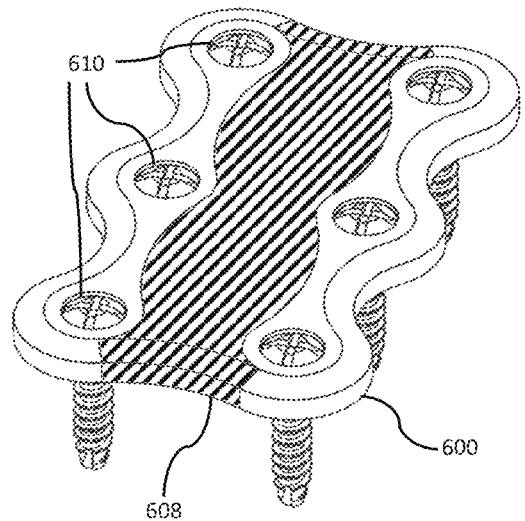
FIG. 6B is a view of the sternal fixation device of FIG. 6A with the threaded fasteners fully seated in the sternal fixation device in accordance with embodiments herein.

FIG. 6A shows a view of the sternal fixation device 600 with elastomeric section 608 and threaded fasteners 610 to engage the threaded holes 606 in the plate sections. FIG. 6B shows sternal fixation device 600 with the threaded fasteners 610 fully seated in the plate sections. The sternal fixation device 600 is intended to be placed on the sternum with the elastomeric section 608 spanning the sternotomy line, and the threaded fixation members 610 are advanced into the holes in the plate sections 602 to rigidly fix the plate to the two halves of the sternum. The threaded fixation members shown are intended to be inserted after a hole is pre-drilled into the sternum, but other embodiments may include self-drilling features. If emergency re-entry is required, the surgeon may use a standard surgical scalpel to bisect the elastomer section 608 between the plate sections without the need for additional instrumentation.

FIGS. 7A, 7B, 7C, and 7D illustrate examples of various embodiments of chest wall repair devices for fixing the sternum and/or a rib segment. FIG. 7A illustrates a sternocostal fixation device, FIG. 7B illustrates a longitudinal fixation device, FIG. 7C illustrates a transverse fixation device, and FIG. 7D illustrates a rib fixation/spanning device. FIG. 7A also shows the flexibility of the rib segment portion, as evidenced by the background gray elements showing alternative configurations.

FIG. 8 illustrates the chest wall repair devices of FIGS. 7A, 7B, 7C, and 7D in example locations on the chest wall.

It is to be understood that the configurations and/or approaches described herein are exemplary in nature, and that these specific embodiments or examples are not to be considered in a limiting sense, because numerous variations are possible. The specific devices or methods described herein can represent one or more of any number of strategies.

The subject matter of the present disclosure includes all novel and nonobvious combinations and subcombinations of the various devices, methods, systems, and configurations, and other features, functions, acts, and/or properties disclosed herein, as well as any and all equivalents thereof.

What is claimed is:

1. A method of orthopedic repair, comprising:
   affixing a bone repair device across a portion of a sternum or a rib, the bone repair device comprising
   two or more plate sections with at least a portion of one plate section configured to be affixed to a sternum or rib segment, the plate sections each having one or more receiving holes for receiving fixation members; and
   a central elastomeric portion adhered to the two or more plate sections, wherein the two or more plate sections are coupled together and spaced apart by the central elastomeric portion.

2. The method of claim 1 further comprising increasing spacing between the plate sections prior to affixing the bone repair device to the sternum to apply compression to the bone repair device.

3. A method of sternal repair permitting rapid reentry, comprising:
   placing a sternal repair device on a sternum across a site of a sternal osteotomy or sternotomy, the sternal repair device comprising two or more plate sections with at least a portion of a first plate section configured to be affixed to a first side of an anterior of the sternum on a first side of the site of the sternal osteotomy or sternotomy, and at least a portion of a second plate section configured to be affixed to a second side of the anterior of the sternum on a second side of the site of the sternal osteotomy or sternotomy, and a central elastomeric portion coupled to and spacing apart the first and second plate sections spanning a central portion of the anterior of the sternum at the site of the sternal osteotomy or sternotomy;
   affixing the first and second plate sections to the sternum, the central elastomeric portion arranged to be cut to provide rapid reentry to the site of the sternal osteotomy or sternotomy.

4. The method of claim 3, wherein the central elastomeric portion arranged to be cut to provide rapid reentry to the site of the sternal osteotomy or sternotomy comprises the central elastomeric portion arranged to be cut by a scalpel to provide rapid reentry to the site of the sternal osteotomy or sternotomy.

5. The method of claim 3, further comprising pre-stretching the central elastomeric portion prior to affixing the first and/or second plate sections to the sternum.

6. The method of claim 3, further comprising increasing spacing between the first and second plate sections prior to affixing the first and/or second plate sections to the sternum to apply compression to the sternum.

7. The method of claim 3, further comprising affixing at least one of the first and second plate sections to one or more ribs.

8. The method of claim 3, wherein at least one of the first and second plate sections comprises one or more hooks, further comprising coupling the one or more hooks around a side of the sternum.

* * * * *